United States Patent [19]
Luitjes et al.

[11] Patent Number: 5,905,115
[45] Date of Patent: May 18, 1999

[54] SUGAR AMINES AND SUGAR AMIDES AND USE AS GLUES

[75] Inventors: Hendrikus Luitjes, Ede; Silvan De Spirt, Wageningen; Augustinus Emmanuel Frissen, Wageningen; Jacobus Van Haveren, Wageningen; Robert Willem Frederik Kammelar, Warnsveld, all of Netherlands

[73] Assignee: Cooperatieve Weiproduktenfabriek "Borculo" W. A., Netherlands

[21] Appl. No.: 08/957,537

[22] Filed: Oct. 29, 1997

[30] Foreign Application Priority Data

Oct. 29, 1996 [NL] Netherlands .................... 1004379

[51] Int. Cl.$^6$ .................... C07H 15/04; C07H 15/12; C07C 235/10
[52] U.S. Cl. .................... 525/54.2; 536/17.9; 528/422
[58] Field of Search .................... 525/54.2; 527/312; 536/17.2, 17.9; 528/422

[56] References Cited

FOREIGN PATENT DOCUMENTS 9222606  12/1992  WIPO .

OTHER PUBLICATIONS

Synthetic Communications, deel 23, nr. 1, Jan. 1, 1993, Bladzijden 35–44, XP000562511 Garelli–Calvet R et al.

Carbohydrate Research, deel 242, 1993, Amsterdam NL, bladzijden 11–20, XP002037492 muller–fahrnow A. et al.

Tetrahedron, ddel 50, nr. 27, Jul. 4, 1994, bladzijden 8103–8116, XP000647742 —Lammers H et al.

*Primary Examiner*—Nathan M. Nutter
*Attorney, Agent, or Firm*—Bachman & LaPointe, P.C.

[57] ABSTRACT

Condensation products having adhesive properties are obtained by reaction of a polyamine with at least two equivalents of an oligosaccharide or a derivative thereof. Examples of the oligosaccharide include glucose, lactose, lactobionic acid and gluconic acid. Examples of the polyamine include diethylene triamine and triethylene tetraamine. The reaction may be a direct amination of the oligosaccharide, with the formation of a glycosylamine and optional N-acylation, or a reductive amination of the oligosaccharide, a glycitylamine being obtained, or alternatively an amidation of an glyconic acid. The condensation products can be used for gluing, for example, paper, cardboard, wood, plastic or glass at low or high temperature.

18 Claims, No Drawings

SUGAR AMINES AND SUGAR AMIDES AND USE AS GLUES

The invention relates to condensation products based on carbohydrates and amines and to the use of these as active component of glue.

The use of carbohydrates such as starch and derivatives thereof as a glue is generally known. The carbohydrates have the advantage, compared with other adhesive polymers, that they are biodegradable. However, handling and processing the carbohydrates having adhesive power is not as convenient as would be desirable. DE-A-1905054 discloses thermosetting mixtures of sugars (such as molasses, sucrose) and a catalyst such as phosphoric acid, which are suitable as a bonding medium in particular for gluing wood, the action of the catalyst giving rise to a polymer structure. These mixtures may, inter alia, contain certain amines as additives.

Surprisingly, it has now been found that condensation products of polyamines and sugars have good adhesive properties. Depending on the structure of the condensation products obtained, they can have the characteristic properties of tackifiers and of binders.

The condensation products according to the invention can be obtained via a reaction of a polyamine with at least two equivalents of an oligosaccharide (sugar) or a derivative thereof. The structure of the condensation products satisfies the formula:

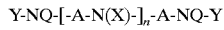

where:

A represents a hydrocarbon group which may be interrupted by an oxygen atom, has 2–8 carbon atoms and, in the case of at least three carbon atoms, may be substituted by a hydroxyl group or a group -NHY;
n=0–10;
Q represents hydrogen, alkanoyl or hydroxyalkyl, or the two groups Q jointly represent a group A;
X represents a group Y, a group -A-NH-Y, an alkanoyl group or a hydroxyalkyl group;
Y represents hydrogen or a group Z, provided that at least two groups Y have the meaning Z; and
Z represents the residue of an oligosaccharide or derivative thereof, whereas two groups having symbol Z may be different.

Desirably, in formula 1
A=CH$_2$—CH$_2$, N=1–4, and Q=H, X=Y

Desirably, also with the proviso that if A is ethylene or 1,3-propylene, n is 0 and Q is hydrogen, then Z is other than a glucose, galactose or mannose residue; and with the proviso that if A is α, ω-C$_6$–C$_8$-alkylene, n is 0 and Q is hydrogen, then Z is other than a gluconic acid or lactobionic acid residue. In addition, desirably wherein A is a C$_2$–C$_6$ alkylene group and Z is a lactose residue or lactobionic acid residue.

The amine component of the compounds according to the invention satisfies formula 3:

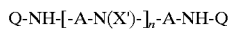

where:

A represents a hydrocarbon group which is possibly interrupted by an oxygen atom, has 2–8 carbon atoms and, in the case of at least three carbon atoms, may be substituted by a hydroxyl group or an amino group;
n=0–10;
Q represents hydrogen or hydroxyalkyl, or the two groups Q jointly represent a group A;

X' represents hydrogen, an -A-NH$_2$ group hydroxyalkyl.

Hydroxyalkyl, in the above, is to be understood as a C$_1$–C$_6$-alkyl group substituted by one or more hydroxyl groups, in particular 2-hydroxyethyl or 2,3-dihydroxypropyl.

Examples of suitable amines are ethylene diamine, diethylene triamine, triethylene tetraamine, tetraethylene pentaamine, tris(2-aminoethyl)amine, 1,2-diaminopropane, 1,3-diaminopropane, hexamethylene diamine, N,N'-bis(2-hydroxyethyl)-1,2-diaminoethane, N,N-bis(2-aminoethyl)-2-aminoethanol, 1,3-diamino-2-propanol, 2,2'-oxybisethylamine, piperazine, 1,4,7-triazonane, aminotriazole, cyclohexylene diamine, phenylene diamine, diaminotoluene, and the like.

In particular, the amine component satisfies formula 3':

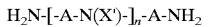

where:
A represents an alkylene group having 2–3 carbon atoms;
n=1–4, especially 1 or 2; and
X' represents hydrogen or a group -A-NH$_2$.

Most preferred are diethylene triamine and triethylene tetraamine.

The oligosaccharide (sugar) component of the compounds according to the invention can be the residue of a reducing mono-, di- or oligosaccharide or alternatively a corresponding reduced residue (glycitol, sugar alcohol) or a corresponding oxidised residue (glyconic, glycuronic, glycaric acid) or another common derivative thereof, or a mixture of oligosaccharides and/or derivatives. An oligosaccharide in the present context is to be understood as a sugar (possibly reduced or oxidised) having a chain length of at most 20 monosaccharide units, in particular at most 8 monosaccharide units. Greatest preference is given to reducing mono, di and trisaccharides, in particular lactose and lactobionic acid. Lactose has a particular advantage in that lactose fractions of varying degrees of purity and varying levels of whey proteins can be used. The whey proteins add to the adhesive properties of the lactose derivatives.

More in particular the oligosaccharide residues satisfy the formula:

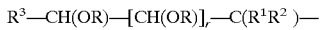

where
r=0–3, in particular 2 or 3;
R, each independently, represents hydrogen, alkyl, substituted alkyl or acyl and one of the groups R may represent an oligosaccharide residue or the formula 2;
R$^1$ represents hydrogen or a group —CH$_2$OR and
R$^2$ represents hydrogen or forms a direct bond with a symbol R linked via 5 or 6 atoms,
or alternatively R$^1$ and R$^2$ together represent oxygen;
R$^3$ represents —CH$_2$OH or —COOH.

Where the symbol R represents alkyl, this is preferably C$_1$–C$_6$ alkyl; substituted alkyl preferably means hydroxy-, C$_1$–C$_4$ alkoxy-, or carboxy-substituted C$_1$–C$_4$ alkyl, especially carboxymethyl; acyl preferably means C$_3$–C$_6$ alkanoyl, hydroxyalkanoyl, carboxyalkanoyl or aralkanoyl, especially acetyl. Where one R represents an oligosaccharide residue, this may also be an oxidised oligosaccharide residue such as HOOC—(CH$_2$OH)$_s$—CH(R$^3$)—O—C(R$^1$)(COOH)—, wherein s is 0 or 1. Preferably R is hydrogen or a monosaccharide residue.

The residue of formula 2 where R$^1$ and R$^2$ jointly represent =O are residues of glyconic acids (sugar acids) (R$^3$=CH$_2$OH), such as gluconic acid, mannonic acid, lactobionic acid, the glyconic acids of the higher galacto-, malto-, cello- and xylo-oligosaccharides, or possibly of glycaric acids (sugar diacids) ($R^3$=COOH), such as tartaric acid and saccharic acid. Preference is given to gluconic acid and especially to lactobionic acid.

The residues of formula 2 where $R^1$ and $R^2$ both represent H are primarily residues of glycitols such as glucitol (sorbitol), xylitol, mannitol, lactitol, maltitol, and the sugar alcohols of the higher galacto-, malto-, cello- and xylo-oligosaccharides.

The residues of formula 2 where $R^2$ forms a direct bond with a symbol R linked via 5 or 6 atoms are furanoside or pyranoside residues, respectively, of primarily glycoses (sugars) such as glucose, galactose, mannose, xylose, arabinose, fructose, lactose, maltose, cellobiose and the corresponding trioses and higher homologues and the like. Preference is given to glucose and especially lactose.

The residues of formula 2 where $R^1$ represents —$CH_2OR$ are residues of ketoses such as fructose or, if $R^2$=H, sorbitol residues and the like.

The compounds with a residue of formula 2 ($R^1$, $R^2$=O) can be prepared in a simple manner via a reaction of 1.5 or more equivalents of the glyconic acid or more preferably the corresponding lactone with the polyamine. Preferentially, 2–4 equivalents of glyconic acids are used, depending on the number of amine functions per polyamine molecule. This amidation reaction proceeds quantitatively, for example at room temperature or slightly elevated temperature in a solvent-free medium or in a solution in water and/or another solvent such as an alcohol.

the compounds with a residue of formula 2 ($R^1$,$R^2$≠O) can be prepared via a reaction of 1.5 or more equivalents of the oligosaccharide with the polyamine in water or an organic solvent, an amino sugar being formed in the process. This amino sugar can be stabilised by acylation, e.g. reacting it with an alkanoyl chloride or anhydride, especially acetyl anhydride. Alternatively, the amino sugar can then, if required, be reduced to a compound with $R^1$=$R^2$=H, for example with sodium borohydride or with hydrogen in the presence of a transition metal as a catalyst. An advantageous variation of this is a reductive amination, the amination and the reduction taking place simultaneously or at least in the same reactor. The oligosaccharide and the amine, together with the catalyst (e.g. palladium on carbon) are combined in a solvent such as water, an alcohol or dimethylformamide, and treated under hydrogen at elevated temperature, for example 20–60° C.

In the process of producing the condensates of the invention as described above, the polyamine may be reacted with two or more different oligosaccharide components if desired, e.g. glucose and lactose, or lactose and lactobionic acid. Thus in formula 1 representing the condensates, the symbols Y and Z may have two or more different meanings within the same molecule. Also, the condensates of the invention may be mixtures of different compounds of formula 1.

The compounds thus obtained have excellent adhesive properties. The invention therefore also relates to the use of these compounds as a glue. The compounds can be used as such or as a solution in a suitable solvent such as water or a (poly)alcohol to form an adhesive composition. These compositions contain a major amount of the compounds of the invention, i.e. preferably at least 10 wt. %, more preferably at least 20 wt. %, up to 90 or even 98 wt. %. The compositions preferably contains thickeners in an amount between 10 and 40 wt. %, such as starch, cellulose, guar and pectins, and common polysaccharide derivatives such as carboxymethylated, oxidised, acetylated derivatives, proteins, such as whey proteins, or thermoplastic polymers such as polyacrylates, polyvinyl alcohols, and ethylene/vinyl acetate copolymers. They may also contain fillers such as clays, silicates, talc, wood flour, or the like. Other suitable components include viscosity/rheology regulators, tackifiers, plasticisers such as glycerol or other polyols, antioxidants, biocides, humectants, wetting agents. The compositions may further contain gluing aids such as (soya) proteins, urea, borax and the like. The adhesive composition can be water-based, i.e. contain at least 25%, in particular 50–90 wt. % of water, optionally combined with solution aids such as alcohols. The compounds can be processed either cold or hot ("hot melt"). In case of hot-melts, the compositions will typically contain little or no water and may then contain a plasticiser, in addition to the further components listed above (thickeners, fillers etc.). The compounds and compositions effect very good adhesion of paper, cardboard, wood, plastic, glass, metals and the like are suitable e.g. for applications such as paper coating, corrugating board and boxes, paper bag manufacturing, laminating adhesives, wall covering adhesives and the like.

EXAMPLE 1

Diethylene Triamine and Gluconic Acid

A stirred solution of 38.6 g (0.37 mol) of diethylene triamine in 600 ml of water was admixed with 200 g (1.12 mol, 3 eq.) of gluconolactone. After 15 hours' stirring at room temperature the reaction mixture was boiled down, a clear oil being obtained. Yield 234.6 g (100%). The product was a glassy material which is suitable as a hot-metal glue, i.e. a glue which can be processed with warming.

EXAMPLE 2

Diethylene Triamine and Gluconic Acid

Example 1 was repeated, except that 133 g of gluconolactone (2 eq.) were used. The product was pliable and resilient glue.

EXAMPLE 3

Triethylene Tetraamine and Gluconic Acid

A stirred solution of 40.9 g (0.28 mol) of triethylene tetraamine in 600 ml of water was admixed with 200 g (1.12 mol, 4 eq.) of gluconolactone. After 15 hours' stirring at room temperature the reaction mixture was boiled down, a clear oil being obtained. Yield 254.8 g (100%). The product binds glass and paper so strongly that they cannot be pulled loose without breaking.

EXAMPLE 4

Diethylene Triamine and Lactose

A stirred solution of 10 g (27. 7 mmol) of lactose in 100 ml of water was admixed, at 60° C., with 1.0 g (3 equivalents) of diethylene triamine. After 15 hours' stirring at 60° C. the reaction mixture was boiled down, a clear resin being obtained. Yield 32.6 g (100%). When heated gently the product becomes syrupy, and it is soluble in water. The product binds glass and paper so strongly that they cannot be pulled loose without breaking.

EXAMPLE 5

Diethylene Triamine and Lactose

A stirred solution of 0.9 g (9.3 mmol) of diethylene triamine in 120 ml of water was admixed with 10 g of spray-dried sweet whey powder (containing 71% lactose and 12.5% whey proteins). The mixture was stirred for 15 hours at 50° C. After evaporation a light brown solid material was obtained.

EXAMPLE 6

Triethylene Tetraamine and Lactose

Lactose (10 g, 27.7 mmol) was dissolved in about 100 ml of water at 0° C. Triethylene tetraamine (1.0 g, 6.93 mmol) was added with stirring. After overnight stirring, the solution was evacuated to yield a yellow solid of about 10 g. A solution of 75–80% by weight constituted an adhesive composition which effectively glues paper. The adhesive force is larger than the force of the paper, as determined by a T-peel test.

EXAMPLE 7

Tetraethylene Pentaamine and Lactose

Lactose (10 g, 27.7 mmol) was dissolved in about 100 ml of water at 0° C. Tetraethylene pentaamine (1.1 g, 5.54 mmol) was added at 0° C. with stirring. After overnight stirring, the solution was evacuated to yield a yellowish, somewhat sticky solid. Yield 10 g. A solution of 75% by weight (dry substance) constituted an adhesive composition which effectively glues paper. The adhesive force is larger than the force of the paper, as determined by a T-peel test.

EXAMPLE 8

Pentaethylene Hexaamine and Lactose

Lactose (10 g, 27.7 mmol) was dissolved in about 100 ml of water at 0° C. Pentaethylene hexaamine (1.1 g, 4.62 mmol) was added after overnight stirring at a temperature between 0 and 20° C. The solution was evacuated to yield a yellow solid of about 10 g. A solution of 75–80% by weight constituted an adhesive composition which effectively glues paper. The adhesive force is larger then the force of the paper, as determined by a T-peel test.

EXAMPLE 9

Diethylene Triamine and Lactose and Gluconic acid

To a stirred solution of 10 g lactose (27.7 mmol, 1 eq.) at 0° C. was added 2.9 g diethylene triamine. After overnight reaction, 9.98 g of gluconolactone (55.4 mmol, 2 eq.) was added. After evaporation, a sirup obtained which was hardly flowable at room temperature. The yield was about 21 g. The product contains 0.5 wt. % of water. The adhesive force of the product as 75–80% by weight (dry substance) in water is comparable to the products of examples 6–8.

EXAMPLE 10

Tris(2-aminoethyl)amine and Lactose

To a stirred solution of 10 g lactose (27.7 mmol) was added 1.2 g of tris(aminoethyl)amine. After overnight reaction, the reaction mixture was evaporated. A brown-yellow solid was obtained in a yield of about 10 g. This product exhibited a satisfactory adhesive force, although somewhat weaker than those of examples 6–9.

EXAMPLE 11

Acetylation of Diethylenetriamine-Lactose Adduct

To 10 g (11.0 mmol) of diethylenetriamine-lactose adduct (product of example 4) was added 100 ml of methanol. Acetic anhydride (3.38 g, 33.0 mmol) was then added with stirring. After the mixture had become homogeneous, the solvents were evaporated. The product was the N-acetylated title adduct.

EXAMPLE 12

Acetylation of diethylenetriamine-Lactose-Gluconic Acid Adduct

To 11.4 g (14.4 mmol) of diethylenetriamine-lactose-gluconic acid adduct (product of example 9) was added 100 ml of methanol. Acetic anhydride (1.47 g; 14.4 mmol) was then added with stirring. After the mixture had become homogeneous, the solvents were evaporated. The product was the N-acetylated title adduct.

We claim:

1. An adhesive compound consisting essentially of a condensation product of (1) a polyamine and (2) at least two equivalents of an oligosaccharide or a derivative thereof as an adhesive.

2. An adhesive compound which satisfies the formula:

$$Y-NQ-[-A-N(X)-]_n-A-NQ-Y \qquad 1$$

where:

A represents a hydrocarbon group which has 2 carbon atoms, or a hydrocarbon group which as 3–8 carbon atoms and which may be interrupted by an oxygen atom and may be substituted by a hydroxyl group or a group -NHY;

n=0–10;

Q represents hydrogen, alkanoyl or hydroxyalkyl, or the two X represents a group Y, a group -A-NH-Y, an alkanoyl group or a hydroxyalkyl group;

Y represents hydrogen or a group Z, provided that at least two groups Y have the meaning Z; and Z represents the residue of an oligosaccharide or derivative thereof, whereas two groups having symbol Z may be different.

3. The adhesive compound of claim 2, wherein the oligosaccharide residue Z satisfies the formula:

$$R^3-CH(OR)-[CH(OR)]_r-C(R^1R^2)- \qquad 2$$

where r=0–3,

R, each independently, represents hydrogen, alkyl, substituted alkyl or acyl and one of the groups R may represent an oligosaccharide residue or the formula 2;

$R^1$ represents hydrogen or a group —$CH_2OR$ and $R^2$ represents hydrogen or forms a direct bond with a symbol R linked via 5 or 6 atoms, or alternatively $R^1$ and $R^2$ together represent oxygen;

$R^3$ represents —$CH_2OH$ or —COOH.

4. The adhesive compound of claim 2, wherein the oligosaccharide residue is a lactose residue or a lactobionic acid residue.

5. The adhesive compound of claim 2, wherein in formula 1

A=$CH_2$—$CH_2$, N=1–4, and Q=H, X=Y.

6. The adhesive compound of claim 2, wherein in the formula 2 r=2 or 3.

7. The adhesive compound of claim 2 wherein Z represents the residue of an oligosaccharide.

8. The adhesive compound of claim 2 wherein Z represents glyconic acid or glycitol derivative thereof.

9. An adhesive composition containing 10–90 wt. % of an adhesive compound of claim 1, together with at least component selected from fillers and thickeners.

10. The composition of claim 9, further containing 25–90 wt. % of water and/or 1–10 wt. % of whey proteins.

11. The composition of claim 9, which is a hot melt and contains 50–90 wt. % of condensation product and a plasticizer.

12. A condensation product complying with the formula:

$$Y-NQ-[-A-N(X)-]_n-A-NQ-Y \qquad 1$$

where:
  A represents a hydrocarbon group which has 2 carbon atoms, or a hydrocarbon group which has 3–8 carbon atoms and which may be interrupted by an oxygen atom and may be substituted by a hydroxyl group or a group -NHY;
  n=0–10;
  Q represents hydrogen, alkanoyl or hydroxyalkyl, or the two X represents a group Y, a group -A-NH-Y, an alkanoyl group or a hydroxyalkyl group;
  Y represents hydrogen or a group Z, provided that at least two groups Y have the meaning Z; and
  Z represents the residue of an oligosaccharide or derivative thereof, whereas two groups having symbol Z may be different.

13. The condensation product of claim 12, wherein A is a $C_2$–$C_6$ alkylene group and Z is a lactose residue or lactobionic acid residue.

14. The condensation product of claim 12 as a adhesive composition.

15. The condensation product of claim 12 wherein Z represents the residue of an oligosaccharide.

16. The condensation product of claim 12, wherein Z represents glyconic acid or glycitol derivative thereof.

17. A process for preparing an adhesive condensation product of a polyamine and at least two equivalents of an oligosaccharide or a derivative thereof, comprising reacting a polyamine of the formula:

$$Q-NH-[-A-N(X')-]_n-A-NH-Q \qquad 3$$

where:
  A represents a hydrocarbon group which may be interrupted by an oxygen atom, has 2–8 carbon atoms and, in the case of at least three carbon atoms, may be substituted by a hydroxyl group or a group -NHY;
  n=0–10;
  Q represents hydrogen, alkanoyl or hydroxyalkyl, or the two groups Q jointly represent a group A;
  X' represents hydrogen, a group -A-$NH_2$ or a hydroxyalkyl group;
  with at least two equivalents of a glyconic acid or glycaric acid or a lactone thereof.

18. A process for preparing an adhesive condensation product of a polyamine and at least two equivalents of an oligosaccharide or a derivative thereof, comprising reacting a polyamine of the formula:

$$Q-NH-[-A-N(X')-]_n-A-NH-Q \qquad 3$$

where:
  A represents a hydrocarbon group which may be interrupted by an oxygen atom, has 2–8 carbon atoms and, in the case of at least three carbon atoms, may be substituted by a hydroxyl group or a group -NHY;
  n=0–10;
  Q represents hydrogen, alkanoyl or hydroxyalkyl, or the two groups Q jointly represent a group A;
  X' represents hydrogen or a group -A-$NH_2$;
  with at least two equivalents of an oligosaccharide, and the reaction product may be reduced either at the same time or subsequently, or the reaction product is acylated with a reactive $C_1$–$C_8$ acylating agent.

* * * * *